United States Patent
Rossi et al.

(10) Patent No.: US 8,424,133 B1
(45) Date of Patent: Apr. 23, 2013

(54) ISO-ROLL TABLE

(76) Inventors: Remo J. Rossi, Sterling, MA (US);
Glenn Capone, Fitchburg, MA (US)

( * ) Notice: Subject to any disclaimer, the term of this patent is extended or adjusted under 35 U.S.C. 154(b) by 92 days.

(21) Appl. No.: 12/932,182

(22) Filed: Feb. 18, 2011

(51) Int. Cl.
*A47B 13/00* (2006.01)

(52) U.S. Cl.
USPC .................................. 5/601; 5/607

(58) Field of Classification Search .............. 5/600, 601, 5/607–611
See application file for complete search history.

(56) References Cited

U.S. PATENT DOCUMENTS

| | | | | |
|---|---|---|---|---|
| 3,947,686 | A * | 3/1976 | Cooper et al. | 378/209 |
| 5,018,712 | A * | 5/1991 | Schaefer | 5/607 |
| 5,020,170 | A * | 6/1991 | Ruf | 5/607 |
| 5,208,928 | A * | 5/1993 | Kuck et al. | 5/608 |
| 6,094,760 | A | 8/2000 | Nonaka et al. | |
| 6,609,260 | B2 * | 8/2003 | Hand et al. | 5/600 |
| 6,640,363 | B1 * | 11/2003 | Pattee et al. | 5/601 |
| 6,681,423 | B2 | 1/2004 | Zachrisson | |
| 6,817,363 | B2 * | 11/2004 | Biondo et al. | 128/845 |
| 6,862,761 | B2 * | 3/2005 | Hand et al. | 5/600 |
| 7,000,271 | B2 | 2/2006 | Varadharajulu | |
| 7,073,222 | B1 | 7/2006 | Skripps | |
| 7,322,059 | B2 * | 1/2008 | Hornbach | 5/607 |
| 2004/0172758 | A1 | 9/2004 | Alakkat | |
| 2005/0015878 | A1 | 1/2005 | Bannister et al. | |
| 2007/0107125 | A1 * | 5/2007 | Koch et al. | 5/600 |
| 2007/0113336 | A1 * | 5/2007 | Sharps | 5/81.1 R |
| 2008/0134435 | A1 * | 6/2008 | Stolze et al. | 5/616 |
| 2012/0248331 | A1 * | 10/2012 | Iwata | 250/453.11 |

OTHER PUBLICATIONS

Stille, Surgical Instruments, Speciality Tables and Super-Cut Scissors, Speciality tables . . . , 2010, Internet, www:hospitalmanagement.net/contractors/surgrical/stille/.

* cited by examiner

*Primary Examiner* — William Kelleher
*Assistant Examiner* — Richard G Davis
(74) *Attorney, Agent, or Firm* — Stan Collier, Esq

(57) ABSTRACT

An improved medical procedure table has motorized elevation, Trendelenburg tilt, floating tabletop with both longitudinal and lateral travel, multi-caster control, and an iso-roll device for the tabletop. The iso-roll device is connected between a roll plate and a cross plate. The iso-roll device includes a pair of iso-roll guide plates, which are mounted laterally to a bottom of the roll plate. Each iso-roll guide plate has an arcuate guide channel therein having an upwards concave shape. A set of cam followers are positioned in both guide channels and travel therein and also fixedly mounted to a base on the cross plate. A center of radius of the arcuate guide channel is approximately 5 inches above the tabletop. Further, mounted between the iso-roll guide plates and to the roll plate is a support guide plate having an arcuate bottom surface.

11 Claims, 8 Drawing Sheets

FIG. 1

ISO-ROLL TABLE

CROSS REFERENCES TO RELATED APPLICATIONS

NA

REFERENCE TO FEDERALLY SPONSORED RESEARCH OR DEVELOPMENT

NA

REFERENCE TO JOINT RESEARCH AGREEMENTS

NA

REFERENCE TO SEQUENCE LISTING

NA

BACKGROUND OF THE INVENTION

1. Field of the Invention

The present invention relates generally to medical tables for medical procedures, and, in particular, relates to tables that are used for vascular and interventional medical procedures, and, in greater particularity, relates to tables having an iso-axis.

2. Description of the Prior Art

Fluoroscopic imaging devices are an important tool for minimally invasive surgical and interventional procedures because they provide a real-time x-ray view of internal anatomical features whether of tissues, bones, or organs. The x-ray images are displayed on a video monitor(s) that is located so as to be viewable by the surgeon or interventionalist during the patient procedure. Mobile fluoroscopic imaging devices (mobile fluoroscopes) are equipped with an x-ray control system; an x-ray image video monitor display stand; and an x-ray source and image receptor which are mounted to a semicircular gantry designed to permit either manual or motorized movement of the gantry in order to position the x-ray source and image receptor around and about the subject patient anatomy. Manual or motorized positioning of the x-ray source and image receptor gantry, relative to the subject anatomy, includes vertical height adjustment, horizontal movement in the longitudinal and lateral directions, orbital rotation around the patient, and cranial-caudal rotation (along the head-to-toe axis). Mobile fluoroscopes are used with a mobile patient table with a cantilevered and radiolucent tabletop that serves to support the patient and allow the x-ray source and image receptor free movement around and about the patient.

During surgical or interventional procedure involving fluoroscopy, an iso-center is defined as the orbital center, or the point about which the x-ray source and image receptor rotate. An object of anatomical interest positioned at the iso-center will remain within the field of view as the imaging system is rotated and re-positioned about the patient. It is thus very important and beneficial to be able to position the anatomical region of interest at such a point of iso-center during the procedure. In some procedures the tabletop must be tilted to provide better access to the patient anatomy. If the anatomical region of interest is placed on the imaging iso-center and the table can provide iso-centric rotation (tilt), the imaging system and/or the table can be rotated without having the region of interest move outside the imaging area.

The fluoroscope gantry or the patient tabletop supporting the patient for such procedures thus must be moved if additional anatomical areas are to be observed. Many of the tables used for these procedures have tabletops that can be moved with many degrees of freedom. Existing tables typically have a point of tabletop tilt rotation that is located under the tabletop; thus as the tabletop is tilted the tabletop is displaced left or right as it swings about an arc with a center of rotation located under the table top and patient. Thus, during fluoroscopic imaging, if the table top is tilted to the left or right a region of interest within the anatomy of a patient will appear to move laterally across the field of view of the imaging system. If the center or axis of rotation could be displaced from a location under the table to a point above it then the table axis of rotation could be placed in a location that would be of benefit relative to the position of key parts of the human anatomy, the spine for example, as well as simultaneously coincident with the axis of rotation of the imaging system. If the table axis of rotation is placed on iso-center along with the region of interest (a section of the spine) then table rotation can be accomplished without causing the region of interest to drift or move out of the field of view.

There are some table designs that utilize complex linkages and mechanisms to create an approximation of an axis of rotation that is located above the table top. In such designs the point of rotation is not fixed though it does exist above the table top and within a patient's anatomy.

The manufacturing of these tables thus should minimize complex mechanical devices providing these many degrees of freedom to reduce the cost of these tables.

Examples of tables are shown in several patents and patent application publications. U.S. Patent Application 2003/0145383 discloses a lateral tilting device using four legs driven by a motorized screw. The top of the legs are attached to the tabletop and the bottom to the support column. U.S. Patent Application 2004/0172758 discloses a table having longitudinal tilt with the ability to provide iso-center tracking. The iso-center being a point at which radiation is provided to the patient by the radiating machine. U.S. Patent Application 2005/0015878 discloses a lateral and longitudinal tilting device. A frame is mounted to a support column. The frame is pivoted on orthogonal axes having two actuators driving the respective frame. The axes of rotation are thus below the tabletop. U.S. Pat. No. 6,094,760 discloses a table having a lateral tilting device. The tabletop has a pair of circular tracks that travel upon rolls thereunder. A driving means is attached to an axle under the tabletop. U.S. Pat. No. 6,681,423 discloses a table with lateral tilt using four legs between a top and bottom frame. A pair of actuators controls the movement of the top frame. U.S. Pat. No. 7,000,271 discloses a C-arm x-ray machine providing x-rays to an iso-center point.

Accordingly, there is a need for an imaging table having an iso-roll axis above the tabletop and located on or substantially close to the iso-center of the imaging system.

SUMMARY OF THE INVENTION

The present invention is directed at a medical table having a tabletop for patient support. The tabletop can move in multi-degrees of freedom to maintain an iso-center during treatment and/or during examination.

The improved medical procedure table has motorized elevation, Trendelenburg tilt, floating tabletop with both longitudinal and lateral travel, multi-caster control, and an iso-roll device for the tabletop. The iso-roll device is connected between a roll plate and a cross plate. The iso-roll device includes a pair of iso-roll guide plates, which are mounted laterally to a bottom of the roll plate. Each iso-roll guide plate has an arc shape guide channel therein having an upwards concave shape. A set of cam followers are positioned within a guide channel and travel therein and also mounted to a base on the cross plate. A center of radius define by the arc shape guide channel is approximately 5 inches above the tabletop (the approximate mid point of a 50 percentile patient thickness). Further, mounted between the iso-roll guide plates and to the roll plate is a guide plate having an arcuate bottom surface. A series of side rollers and bottom rollers securely contain the guide plate. A linear actuator and a gas spring rod are mounted parallel to each other to the roll plate and the cross plate. The gas spring rod is used to tension the assembly and eliminate lash. The linear actuator moves the roll plate as commanded so that the roll plate with the tabletop thereon moves laterally about the center of radius, or iso-axis. The lateral tilt provided is approximately ±12 degrees.

A preferred embodiment of the present invention is to provide an improved imaging table for radiology procedures.

Another feature of the present invention is to provide an improved imaging table for radiology procedures involving vascular and interventional medical procedures.

It is a further feature of the present invention to provide an improved imaging table having an iso-roll lateral tilt device.

It is still a further feature of the present invention to provide an improved imaging table having a lateral tilt device with an iso-center and iso-axis above the tabletop.

It is still a further feature of the present invention to provide an improved imaging table having a lateral tilt device with an iso-axis above the tabletop wherein the tabletop rotates about the iso-axis during movement.

It is yet a further feature of the present invention to provide an improved imaging table having a lateral tilt device with an iso-axis about the tabletop and constructed in a manner to minimize costs and having a minimum of mechanical parts and still providing patient stability, flexibility in use, and high imaging capabilities.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION OF THE PREFERRED EMBODIMENTS

The present invention is directed at an imaging table used for various medical procedures, in particular, vascular and interventional procedures.

Figure 1:
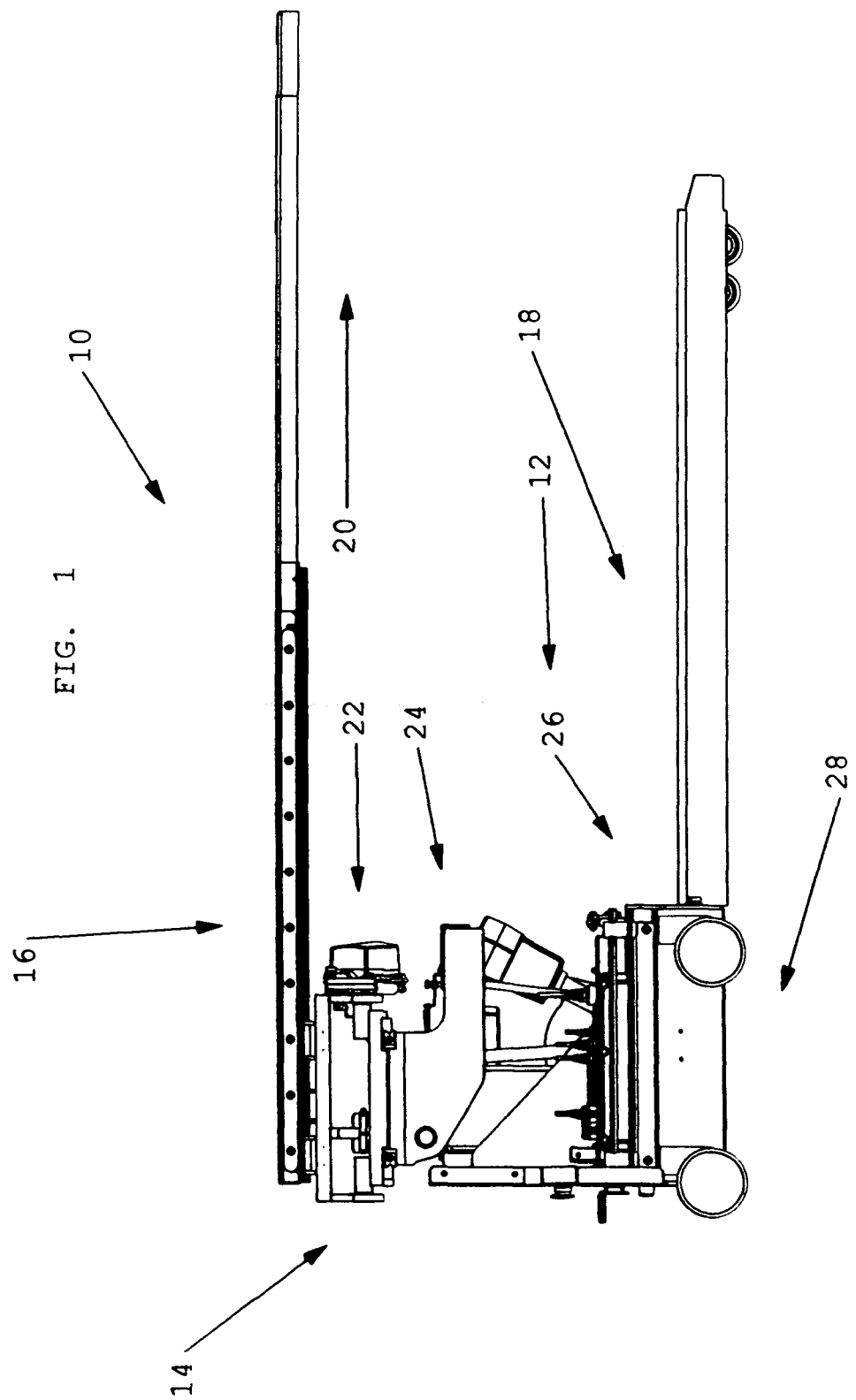
FIG. 1 is right side view of the table of the present invention with the cover removed, the right side being on the right when viewed from the left or foot end, FIG. 1, of the table where the feed are normally positioned.

Turning to the drawings, wherein like components are designated by like reference numerals throughout the various figures, attention is initially directed to FIG. 1 being a right side view of a table 10 of the present invention with a cover, not shown, removed from a support column 12 that is attached to a base 18; the right side being on the right when viewed from the left or foot end 14 of the table 10 where the feet are normally positioned on a tabletop 16. It should be understood that a longitudinal direction is parallel to arrow 20 and that a lateral direction is perpendicular thereto.

The present invention is sold by Image Diagnostics, Inc., of Fitchburg, Mass., as the Aspect ISR model and may be viewed at the website of www.imagediagnostics.com as of the filing date herein. The table 10 has a 4-way floating tabletop 16, an iso-roll device 22, a Trendelenburg feature 24, and motorized elevation 26, controlled by a hand control, not shown. The features of the 4-way floating tabletop 16, the Trendelenburg feature 24, and the motorized elevation 26 are all considered to be of conventional design and shown by one or more of the above patents which are incorporated by reference. The table 10 has a cantilevered, carbon fiber tabletop 16 for improved imaging with an approximate size of 2 by 7 feet with an imaging length of 5 feet. The tabletop 16 is cantilevered off of the support column 12 such that a C-arm x-ray source and x-ray imager can be positioned around the tabletop near the overhang. The table 10 has an adjustable elevation from about 33 to 43 inches, a Trendelenburg tilt of ±12 degrees, a 4-way manual floating tabletop 16 with a hand controller, not shown, where the tabletop 16 has a longitudinal travel of about 32 inches and a transverse or lateral travel of 8 inches, and with multi-casters 28 having total lock, total unlock, and steering lock through the center casters. The table 10 weights approximately 600 pounds and operates with selectable voltage of 120 or 230 VAC, with a battery backup.

Figure 2:
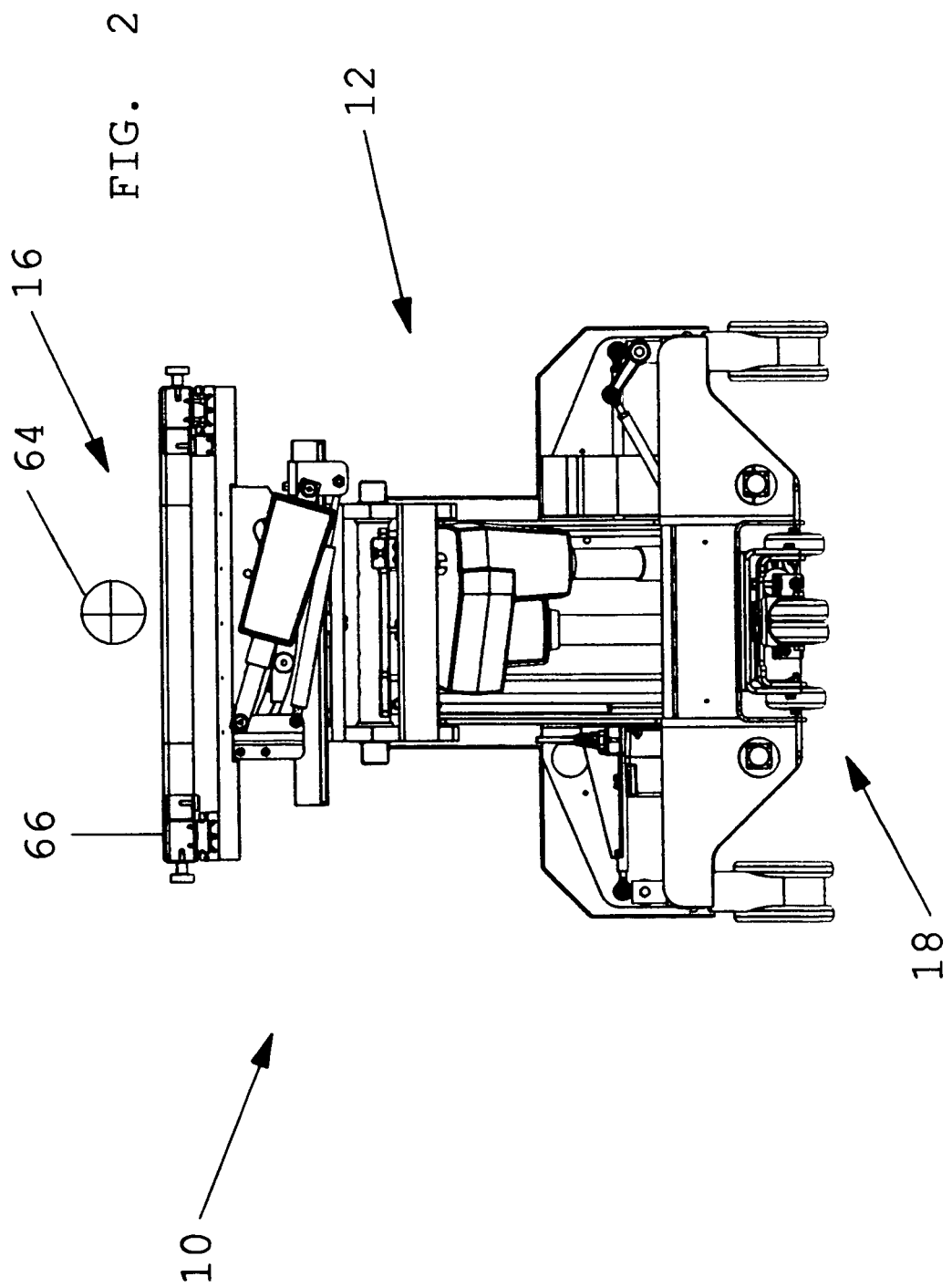
FIG. 2 is a front or head end view of the table of FIG. 1 of the present invention.
Figure 3:
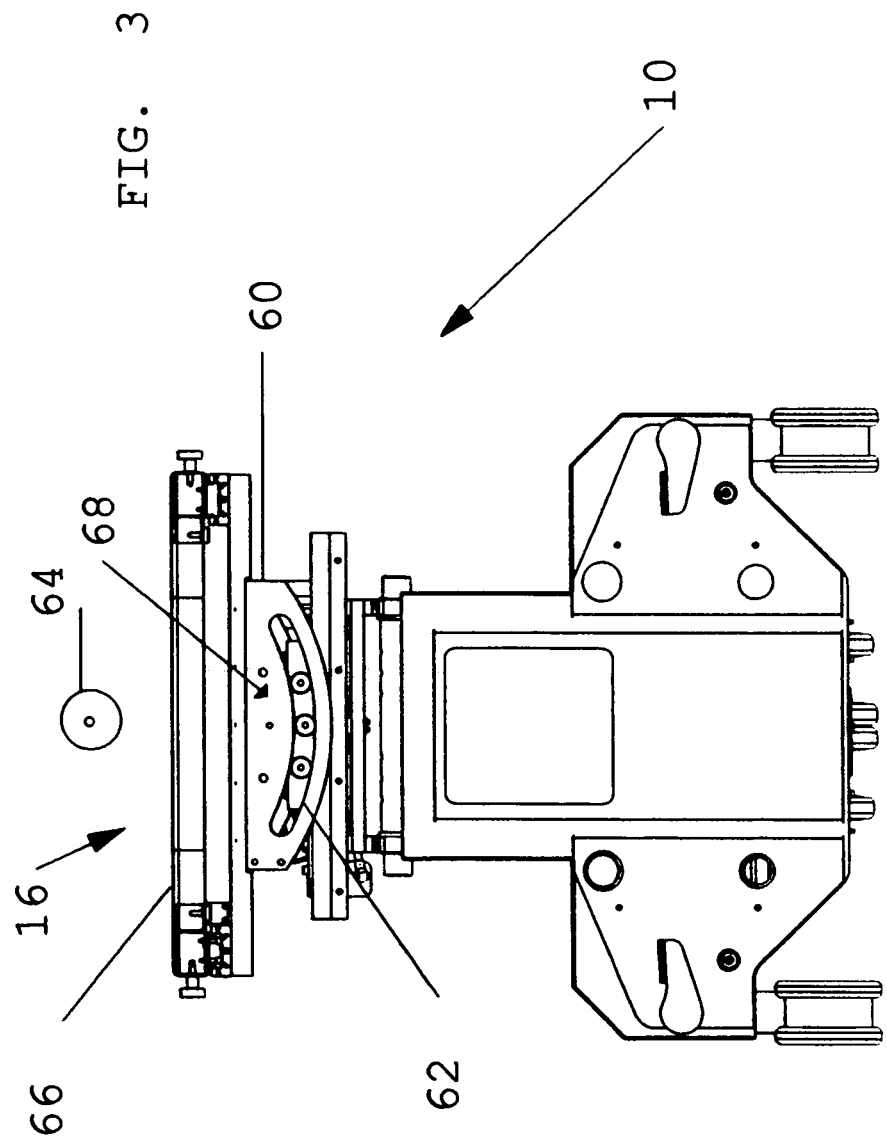
FIG. 3 is an rear or foot end view of the table of FIG. 1 of the present invention.

FIG. 2 is a front end view of the table 10 as seen in FIG. 1. FIG. 3 is a read end view of the table 10 as seen in FIG. 1. The front end being the head end and the rear end being the foot end of the tabletop 16.

Figure 4:
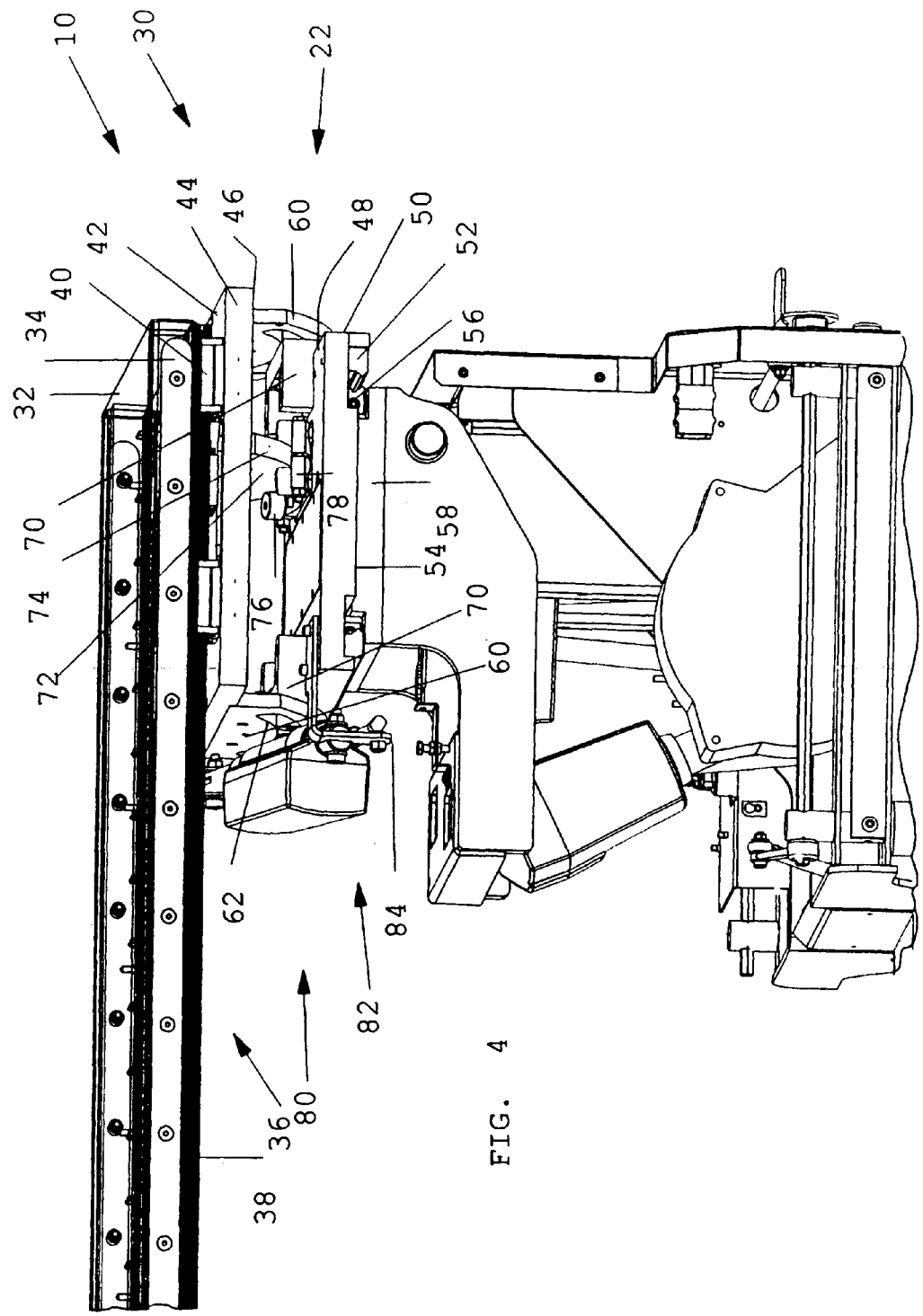
FIG. 4 is a left side view looking down at the iso-roll device of the table of FIG. 1 of the present invention.

It should be understood that the particular iso-roll device 22 shown is one example of accomplishing the features of the present invention. Turning to FIG. 4, a top 30 of table 10 is shown from the left side looking slightly down into the iso-roll device 22. The tabletop 16 has a frame 32 to which a pair side rails 34 are mounted. Mounted to a bottom 36 of the tabletop 16 is a pair of longitudinal rails 38. The tabletop rails 38 slide in tabletop rail guides 40 secured to a top 42 of a roll plate 44. The iso-roll device 22 is connected to a bottom 46 of the roll plate 44 and a top 48 of a cross plate 50. The cross plate 50 has a pair of traverse/lateral rails 52 that are mounted upon a bottom 54 and to a set of lateral rail guides 56 mounted on a top of a Trendelenburg plate 58. It should be understood that the components noted above may be made of machined aluminum and alloys thereof, for example, although other metal would be suitable but more expense. The parts are further attached by means of machine screws and/or bolts and nuts of high quality.

The iso-roll device 22 includes a pair of iso-roll guide plates 60 that are mounted laterally to the bottom 46 of the roll plate 44. Each iso-roll guide plate 60 is mounted perpendicular to the roll plate 44. Each iso-roll guide plate 60 has an arcuate guide channel 62 therein having an upwards concave shape having a center of radius that places the iso-axis 64, FIGS. 2 and 3, approximately 5 inches above a surface 66 of the tabletop 16. A set of support rollers or cam followers 68, FIG. 3, three in each guide channel 62, for example, are positioned in the guide channel 62 and travel therein and also mounted to a base plate 70. The base plate 70 is fixedly attached to the cross plate 50. For further support to the tabletop 16 which may hold a patient weighing up to 450 pounds, for example, a support guide plate 72 is mounted perpendicular between the iso-roll guide plates 60 and to the roll plate 44 and has an arcuate bottom surface 74 that is similarly shaped in curvature as the arcuate channel 62. A series of side rollers 76 and bottom rollers 78 contain/hold the support guide plate 72 at the bottom thereof and the rollers 76 and 78 are also mounted to the cross plate 50. Appropriate sensors may be mounted in the iso-roll device 22 to monitor movement of the support guide plate 72, i.e., the tilt thereof.

Figure 5:
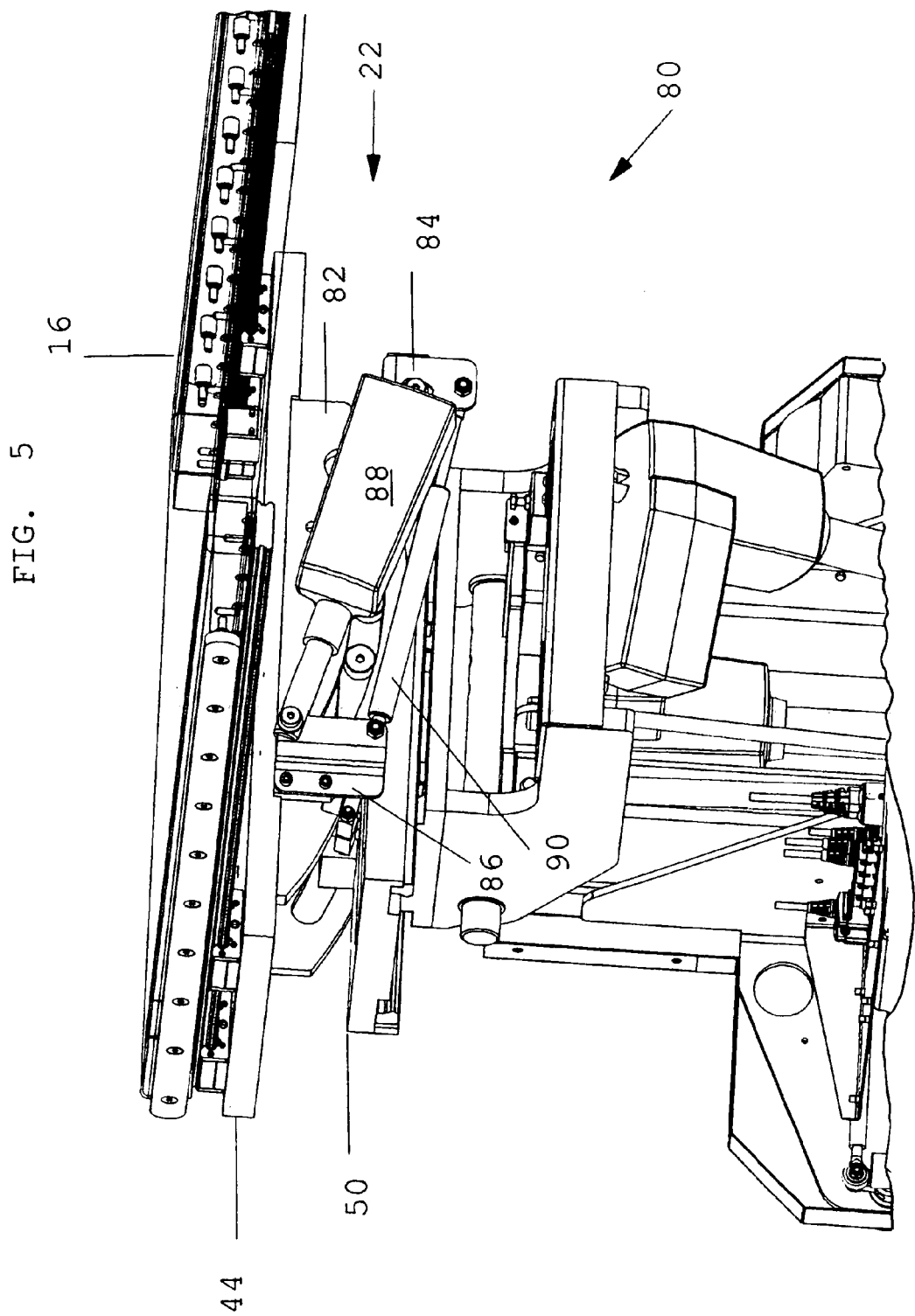
FIG. 5 is a right side view looking up at the iso-roll device of the table of FIG. 1 of the present invention.

Referring to FIG. 5, the roll plate 44 is tilted by a driver device 80 that provides rotation and stability to the tabletop 16. The driver device 80 is position on the head side 82 of the iso-roll device 22. A lower end of the driver device 80 is secured to the cross plate 50 by a lower bracket 84 and to the roll plate 44 by an upper bracket 86. Secured to each bracket in parallel are a linear actuator 88 and a gas-spring rod 90. This combination provides the force to move the cross plate 44 and stability to the tabletop since any lash in the actuator 88 is taken up by the gas spring rod. The driver device 80 moves the roll plate 44 as commanded so that the roll plate 44 with the tabletop 16 thereon moves laterally about a center of radius, or iso-axis 64. The lateral tilt provided is approximately ±12 degrees.

Figure 6:
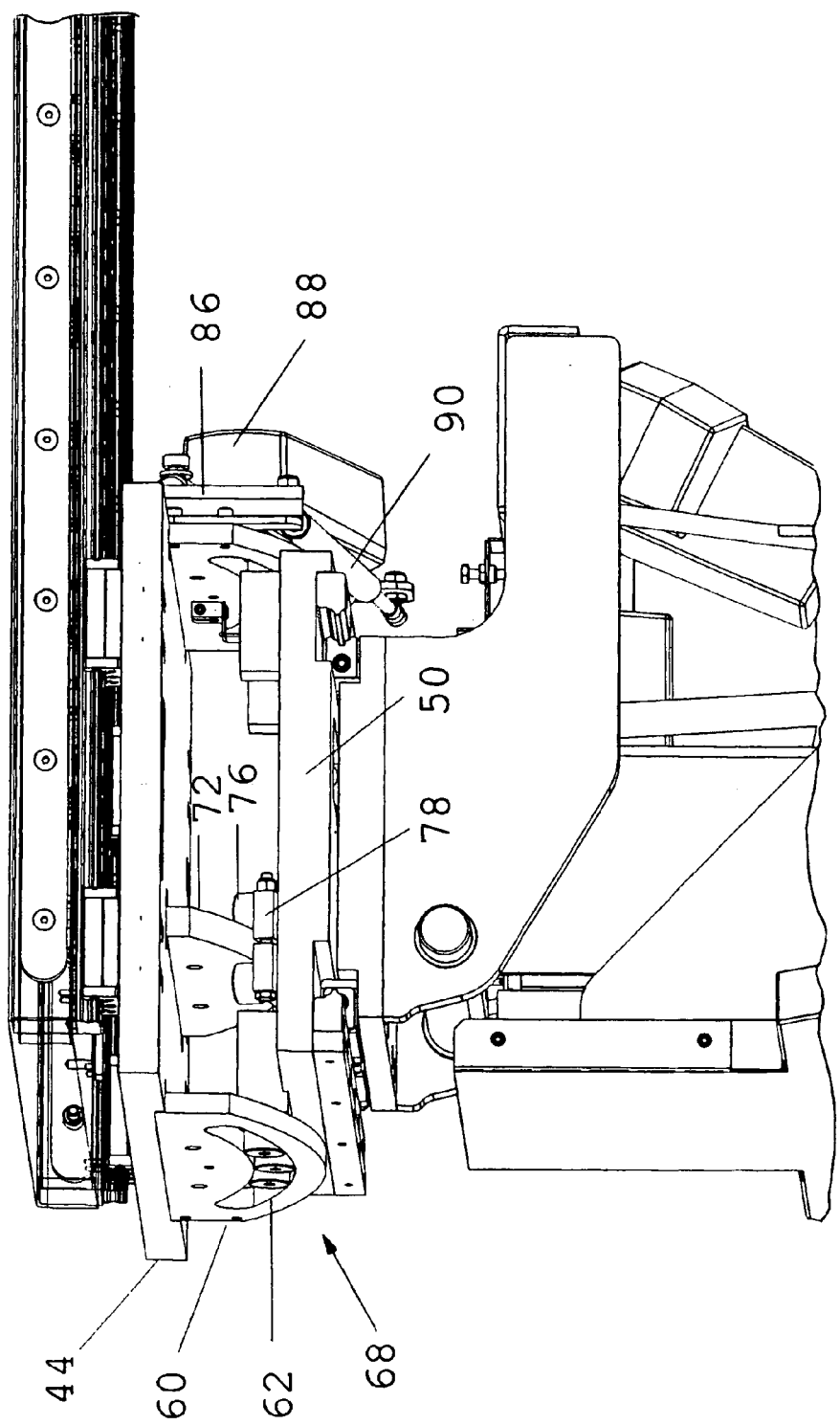
FIG. 6 is a right side view looking back at the iso-roll device of the table of FIG. 1 of the present invention.
Figure 7:
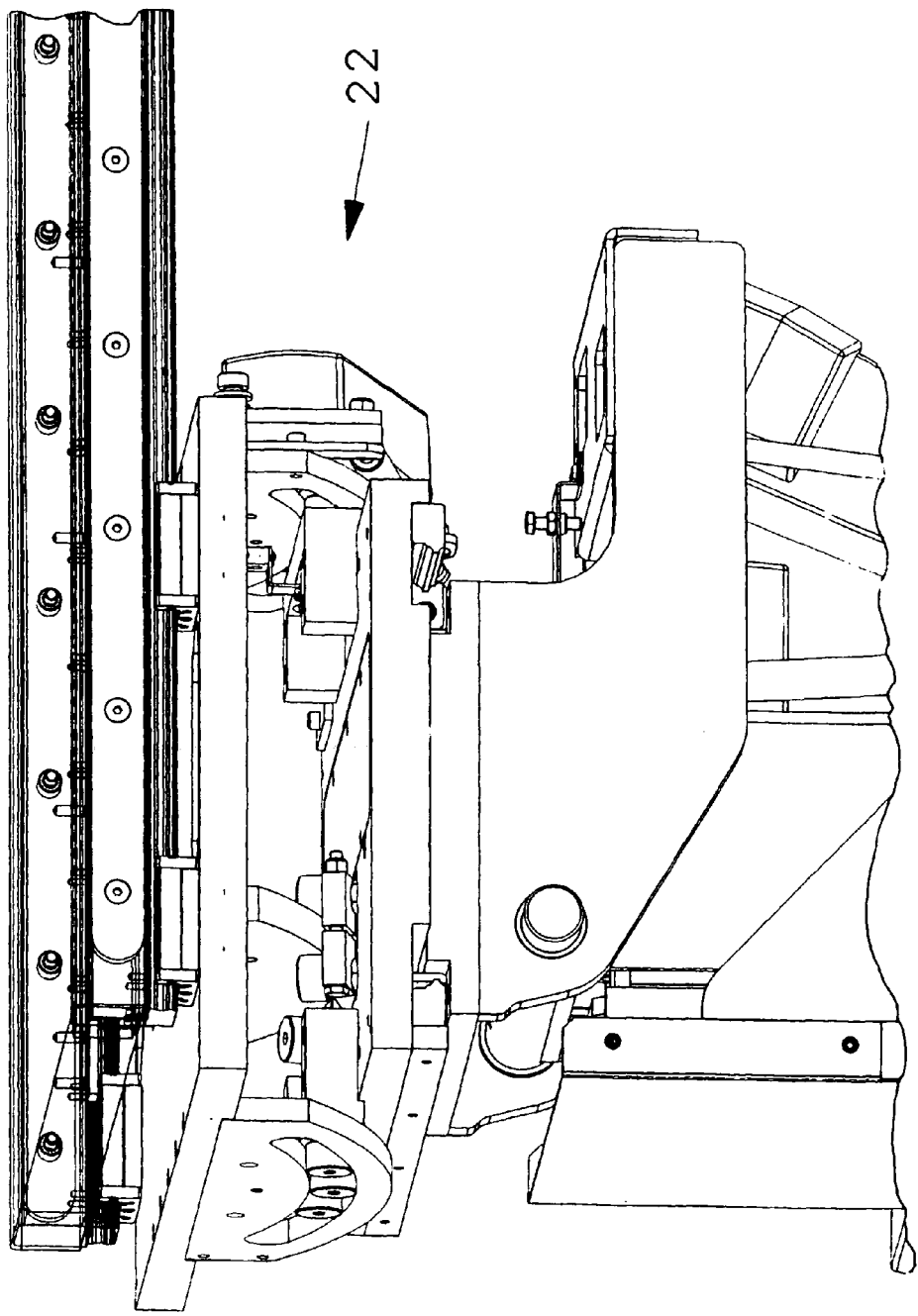
FIG. 7 is a right side view looking forward at the iso-roll device of the table of FIG. 1 of the present invention.
Figure 8:
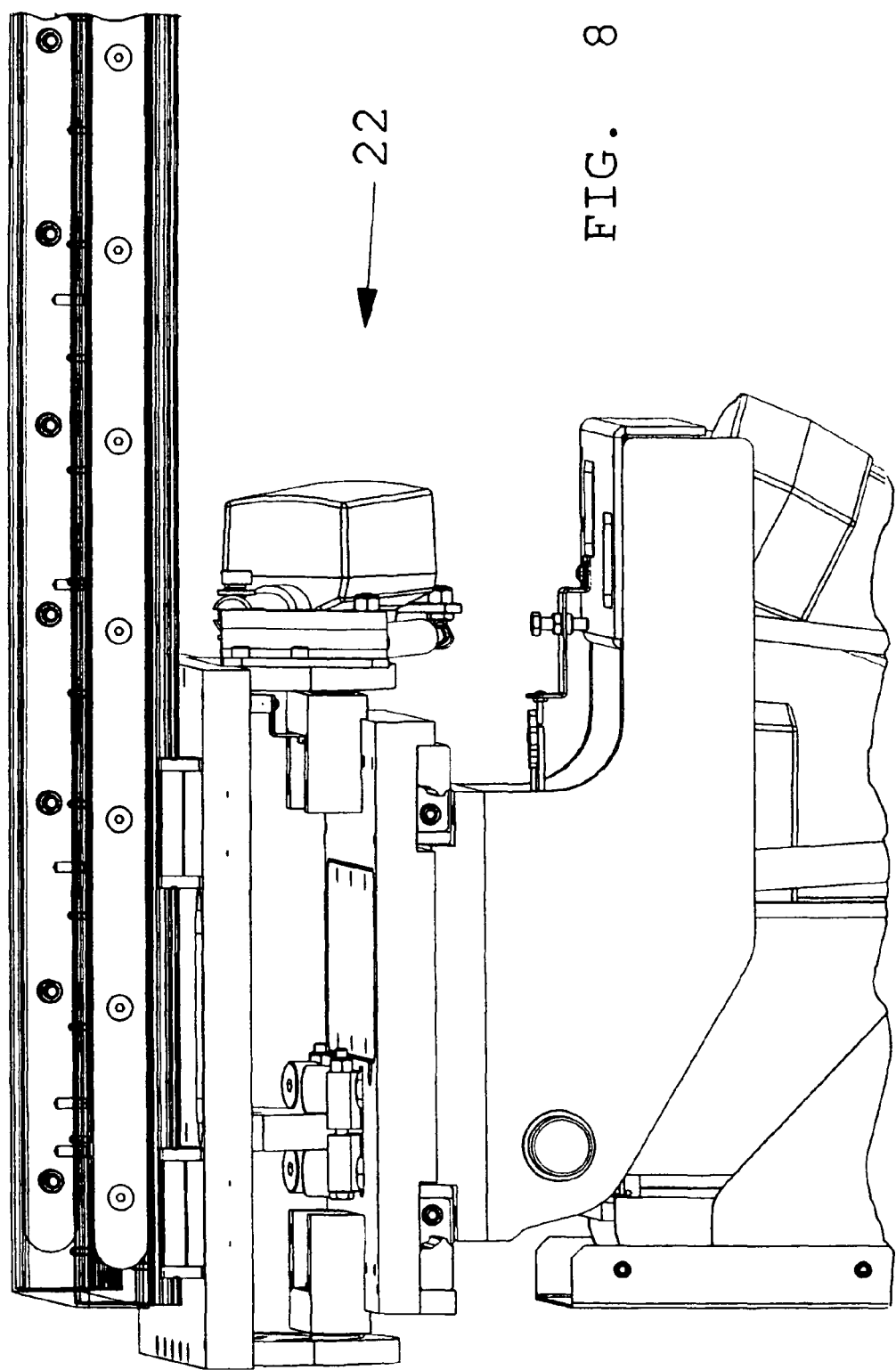
FIG. 8 is a right view looking down into the iso-roll device of the table of FIG. 1 of the present invention.

FIGS. 6 to 8 provide additional views of the iso-roll device 22 for a further understanding of the workings therein.

Since many modifications, variations, and changes in detail can be made to the described embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A table for medical procedures, said table comprising:
   a tabletop;
   a support column, said support column operatively connected to said tabletop, said tabletop being cantilevered thereon, said support column including:
      means for adjustably moving said tabletop in a medically operative procedure, said means for adjustable moving comprising:
         an iso-roll device, wherein said iso-roll device is mounted between plates having longitudinal and lateral rails/rail guides thereon; and
   a base, said base connected to said support column, said base including transporting means.

2. The table for medical procedures as defined in claim 1, wherein an upper plate is a roll plate and the lower plate is a cross plate.

3. The table for medical procedures as defined in claim 2, wherein said iso-roll device comprises:
   a pair of guide plates, each guide plate being mounted to the roll plate, each guide plate having an arcuate channel therein having a center of radius such that an iso-axis is located above the tabletop and is parallel to the longitudinal direction;
   a support guide plate, said support guide plate being mounted to the roll plate, said guide plate having an arcuate bottom surface;
   a plurality of cam followers, said cam followers traveling within said arcuate channels of the guide plates, said cam followers being fixedly mounted to a cross plate;
   a plurality of rollers in rolling contact with the sides of said support guide plate and the bottom arcuate surface of said support guide plate to insure stability of the roll plate, said plurality of rollers fixedly attached to the cross plate; and
   a driver, said driver moving the roll plate in a tilting manner as required by an operator, said driver being operatively attached to said roll plate and said cross plate.

4. The table for medical procedures as defined in claim 3, wherein said iso-axis is located approximately between 2 and 12 inches from the tabletop surface.

5. The table for medical procedures as defined in claim 4, wherein said iso-axis is located approximately 5 inches from the tabletop surface.

6. The table for medical procedures as defined in claim 3, wherein said driver comprises:
   a linear actuator; and
   a gas spring rod.

7. An improved table for medical procedures, the improved table comprising:
   an iso-roll device, said iso-roll device being able to rotate a tabletop about an iso-axis being longitudinally located above the tabletop surface, wherein said iso-roll device comprises:
   a pair of guide plates, each guide plate being mounted to a roll plate, each guide plate having an arcuate channel therein having a center of radius such that an iso-axis is located above the tabletop and is parallel to a longitudinal direction;
   a support guide plate, said support guide plate being mounted to a roll plate, said guide plate having an arcuate bottom surface;
   a plurality of cam followers, said cam followers traveling within said arcuate channels of the guide plates, said cam followers being fixedly mounted to a cross plate;
   a plurality of rollers in rolling contact with the sides of said support guide plate and the bottom arcuate surface of said support guide plate to insure stability of the roll plate, said plurality of rollers fixedly attached to the cross plate; and
   a driver, said driver moving the roll plate in a tilting manner as required by an operator, said driver being operatively attached to said roll plate and said cross plate.

8. The improved table as defined in claim 7, wherein said driver comprises:
   a linear actuator; and
   a gas spring rod.

9. A process for controlling an iso-center location for a patient located on a tabletop of a table for medical procedures as defined in claim 1, said process comprising the steps of:
   identifying the iso-center location of a radiology device;
   placing the patient on the tabletop wherein the iso-center is located within the patient at a desired location;
   locating an iso-axis of the iso-roll device in the iso-center of the radiology device; and
   performing a medical procedure by moving the tabletop wherein the iso-axis remains located in the iso-center.

10. The process as defined in claim 9, wherein the iso-axis is located approximately 2 to 12 inches from a tabletop surface.

11. The process as defined in claim 10, wherein the iso-axis is preferably located approximately 5 inches from the table-top surface.

\* \* \* \* \*